US00PP21060P2

(12) United States Plant Patent

Klemm et al.

(10) Patent No.: US PP21,060 P2

(45) Date of Patent: Jun. 8, 2010

(54) *CALIBRACHOA* PLANT NAMED 'KLECA08178'

(50) Latin Name: ***Calibrachoa* hybrid**
Varietal Denomination: KLECA08178

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,543

(22) Filed: Mar. 25, 2009

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L Bell
(74) *Attorney, Agent, or Firm*—Jondle & Associates, P.C.

(57) ABSTRACT

A new *Calibrachoa* plant named 'KLECA08178' particularly distinguished by dark blue flowers, very good branching, and a mounding and trailing growth habit, is disclosed.

1 Drawing Sheet

Genus and species: *Calibrachoa* hybrid.
Variety denomination: 'KLECA08178'.

BACKGROUND OF THE NEW PLANT

The present invention comprises a new and distinct cultivar of *Calibrachoa,* botanically known as *Calibrachoa* hybrid and hereinafter referred to by the cultivar name 'KLECA08178'. The new cultivar originated from a hybridization made in Summer 2005 in Stuttgart, Germany. The female parent was the proprietary *Calibrachoa* plant 'X 117' (unpatented), while the male parent was the proprietary *Calibrachoa* plant 'CA050580' (unpatented).

The new cultivar was first propagated in May 2006 by vegetative cuttings in Stuttgart, Germany and has been asexually reproduced by vegetative cuttings in Stuttgart, Germany over a two and one-half year period. The present invention has been found to retain its distinctive characteristics through successive asexual propagations.

Plant Breeder's Rights for this cultivar have been applied for in Switzerland on Aug. 5, 2008 and in Canada on Jan. 31, 2008. 'KLECA08178' has not been made publicly available more than one year prior to the filing date of this application.

SUMMARY OF THE INVENTION

The following are the most outstanding and distinguishing characteristics of this new cultivar when grown under normal horticultural practices in Stuttgart, Germany.

1. Dark blue flowers;
2. Very good branching; and
3. A mounding and trailing growth habit.

DESCRIPTION OF THE PHOTOGRAPH

This new *Calibrachoa* plant is illustrated by the accompanying photograph which shows flowers and foliage of the plant; the colors shown are as true as can be reasonably obtained by conventional photographic procedures.

The photograph is of a five-month-old *Calibrachoa* plant, grown in a greenhouse in Stuttgart, Germany, between January and May 2008.

DESCRIPTION OF THE NEW CULTIVAR

The following detailed descriptions set forth the distinctive characteristics of 'KLECA08178'. The data which defines these characteristics were collected from asexual reproductions carried out in Stuttgart, Germany. The plant history was taken on five-month-old plants which were planted as rooted cuttings in 11-cm pots between January and May 2008 and then grown in a greenhouse. The plants had one terminal pinch one week after potting. Color readings were taken under natural light. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Solanaceae.
- *Botanical.*—*Calibrachoa* hybrid.
- *Common.*—*Calibrachoa.*

Parentage:
- *Female.*—The proprietary *Calibrachoa* plant 'X 117' (unpatented), having dark blue flowers.
- *Male.*—The proprietary *Calibrachoa* plant 'CA050580' (unpatented), having pink-purple flowers.

Growth:
- *Form.*—Mounding.
- *Habit.*—Trailing.
- *Height* (*measured from the top of the soil*).—6.0 cm.
- *Width* (*horizontal plant diameter*).—16.0 cm.
- *Time to produce a finished flowering plant.*—10 weeks.
- *Outdoor plant performance.*—Very healthy, continuous flowering.
- *Time to initiate and develop roots.*—16 days.
- *Root description.*—Moderate density, freely branching with white roots.

Stems:
- *Length of basal branches.*—8.0 cm.
- *Internode length.*—0.8 cm to 1.6 cm.

*Diameter of branches* (*from midpoint*).—Primary branches are 6.0 cm. Secondary branches are 2.0 cm.
*Stem color.*—RHS 145A.
*Texture.*—Smooth.
*Pedicel.*—Color: RHS 144B. Length: 1.2 cm. Diameter: 0.2 cm. Texture: Smooth. Anthocyanin: Present, RHS 181C.

Leaves:
*Arrangement.*—Alternate.
*Size.*—Length: 0.7 cm to 2.5 cm. Width: 0.2 cm to 0.6 cm.
*Shape.*—Lanceolate to elliptic.
*Apex.*—Broadly acute.
*Base.*—Attenuate.
*Margin.*—Entire.
*Color.*—Immature: Upper surface: RHS 137D. Lower surface: RHS 138B. Mature: Upper surface: RHS 137A. Lower surface: RHS 137B.
*Texture* (*both surfaces*): Smooth.
*Venation pattern.*—Pinnate.
*Venation color.*—Upper surface: RHS 144A. Lower surface: RHS 144B.
*Petioles.*—Absent.

Flower bud:
*Shape.*—Irregular to oblong.
*Size.*—Length: 2.5 cm. Diameter: 0.5 cm.
*Color at tight bud.*—RHS 79A.

Inflorescence:
*Blooming habit.*—Continuous flowering during summertime.
*Inflorescence type.*—Single.
*Floret type.*—Funnel-shaped.
*Lastingness of individual blooms on the plant.*—7 days.
*Fragrance.*—Absent.

Flowers:
*Immature flower.*—Diameter: Horizontal: 2.8 cm. Vertical: 2.7 cm. Color: Upper surface: RHS 86B. Lower surface: RHS 87B.
*Mature flower.*—Diameter: Horizontal: 3.0 cm. Vertical: 3.2 cm. Color: Upper surface: RHS 86A. Lower surface: RHS 87A.
*Corolla tube.*—Color inside: RHS 4B. Color outside: RHS 87B. Tube length: 1.4 cm. Outside texture: Smooth,
*Petals.*—Apex: Obverse. Base: Fused into the tube. Margin: Entire. Waviness of petals: Weak. Lobation: Weak. Texture (both surfaces): Smooth.
*Sepals.*—Calyx (form): Rosette. Shape: Lanceolate to elliptic. Apex: Acute. Base: Tube fused into the base. Margin: Entire. Length: 1.4 cm. Width: 0.3 cm. Color: Upper surface: RHS 138A. Lower surface: RHS 138B. Texture (both surfaces): Smooth.

Reproductive organs:
*Stamens.*—Number: 5. Filament color: RHS 154A. Filament length: 0.7 cm. Filament diameter: 0.1 cm. Pollen color: RHS 11A. Pollen quantity: Moderate.
*Pistils.*—Number: 1. Length: 0.4 cm. Diameter: 0.2 cm. Stigma color: RHS 149A. Style color: RHS 149A.

Fruit and seed set: No seed set observed.

Disease and insect resistance: No particular resistance or susceptibility has been observed.

COMPARISON WITH PARENTAL AND COMMERCIAL CULTIVARS

'KLECA08178' differs from the female parent 'X 117' (unpatented) in that 'KLECA08178' has dark blue flowers and a trailing growth habit, while 'X 117' has larger dark blue flowers and a semi-upright growth habit.

'KLECA08178' differs from the male parent 'CA050580' in that 'KLECA08178' has dark blue flowers and a trailing growth habit, while 'CA050580' has pink-purple flowers and a flat-trailing growth habit.

'KLECA08178' differs from the commercial cultivar 'KLEC00070' (U.S. Plant Pat. No. 13,394) in that 'KLECA08178' has larger flowers and more branching, while 'KLEC00070' has smaller flowers and less branching.

I claim:

1. A new and distinct cultivar of *Calibrachoa* plant named 'KLECA08178' as shown and described herein.

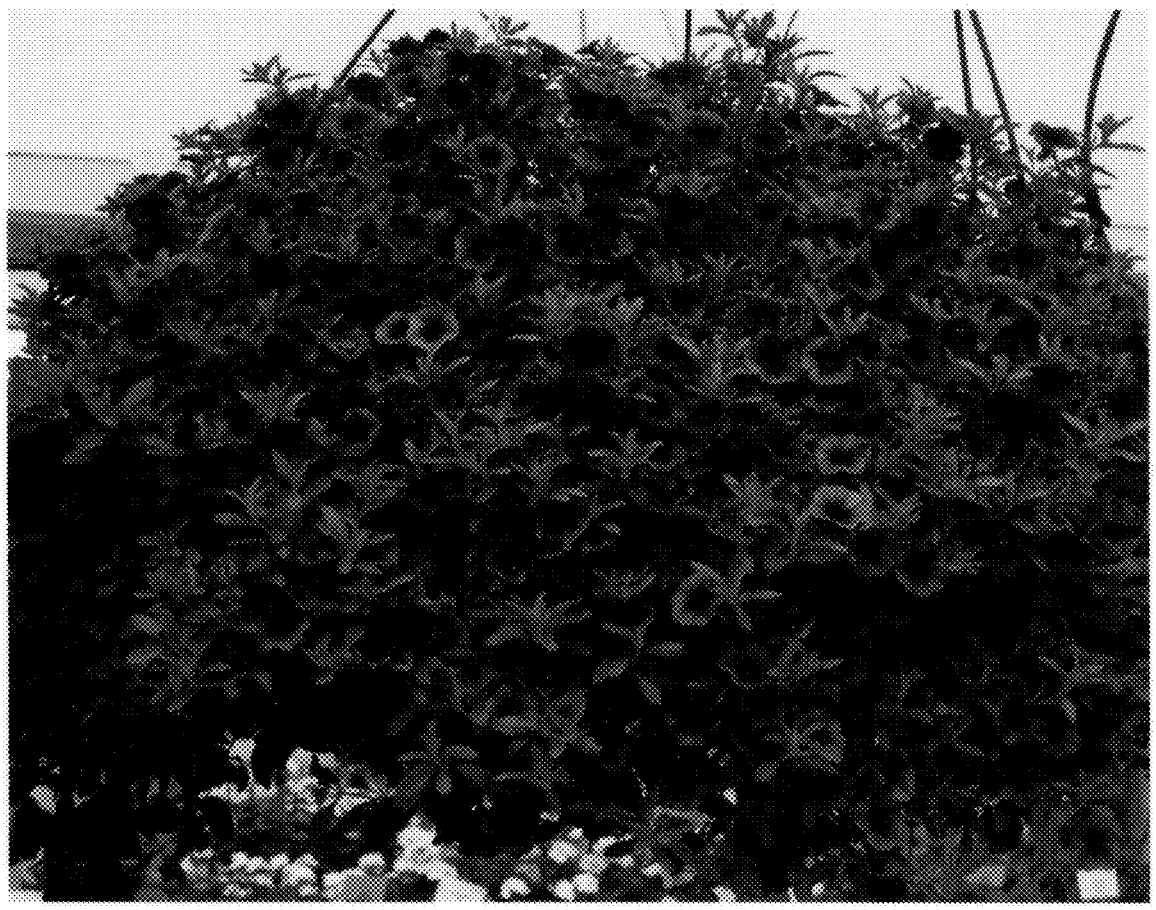

* * * * *